(12) United States Patent
Kinsella et al.

(10) Patent No.: US 6,500,130 B2
(45) Date of Patent: Dec. 31, 2002

(54) STEERABLE GUIDEWIRE

(75) Inventors: Bryan Kinsella, Seattle, WA (US); Lucas Gordon, Redmond, WA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 49 days.

(21) Appl. No.: 09/746,701

(22) Filed: Dec. 21, 2000

(65) Prior Publication Data

US 2002/0082523 A1 Jun. 27, 2002

(51) Int. Cl.⁷ .............................................. A61M 25/09
(52) U.S. Cl. ...................................................... 600/585
(58) Field of Search ........................................ 600/585

(56) References Cited

U.S. PATENT DOCUMENTS

| | | |
|---|---|---|
| 419,926 A | 1/1890 | Chapman |
| 3,416,531 A | 12/1968 | Edwards |
| 3,547,103 A * | 12/1970 | Cook .......................... 600/585 |
| 3,879,516 A | 4/1975 | Wolvek ....................... 264/135 |
| 4,003,369 A * | 1/1977 | Heilman et al. ............. 600/585 |
| 4,425,919 A | 1/1984 | Alston, Jr. et al. |
| 4,516,972 A | 5/1985 | Samson ....................... 604/282 |
| 4,548,206 A | 10/1985 | Osborne |
| 4,569,347 A | 2/1986 | Frisbie |
| 4,657,024 A | 4/1987 | Coneys |
| 4,676,249 A * | 6/1987 | Arenas et al. ............... 600/585 |
| 4,719,924 A | 1/1988 | Crittenden et al. |
| 4,795,439 A | 1/1989 | Guest ........................... 604/43 |
| 4,886,067 A * | 12/1989 | Palermo |
| 4,960,410 A | 10/1990 | Pinchuk ....................... 604/96 |
| 5,040,543 A * | 8/1991 | Badera et al. |
| 5,057,092 A | 10/1991 | Webster, Jr. ................. 604/282 |
| 5,059,183 A * | 10/1991 | Semrad ........................ 600/585 |
| 5,060,660 A * | 10/1991 | Gambale et al. ............. 600/585 |
| 5,222,949 A | 6/1993 | Kaldany ...................... 604/282 |
| 5,279,596 A | 1/1994 | Castaneda et al. .......... 604/282 |
| 5,329,923 A | 7/1994 | Lundquist |
| 5,334,171 A | 8/1994 | Kaldany ...................... 604/282 |
| 5,378,234 A | 1/1995 | Hammerslag et al. ......... 604/95 |
| 5,381,782 A | 1/1995 | DeLaRama et al. |
| 5,437,827 A | 8/1995 | Marx ........................... 264/103 |
| 5,460,608 A | 10/1995 | Lodin et al. .................. 604/96 |
| 5,477,856 A | 12/1995 | Lundquist |
| 5,531,719 A | 7/1996 | Takahashi .................... 604/280 |
| 5,573,520 A | 11/1996 | Schwartz et al. ........... 604/282 |
| 5,599,326 A | 2/1997 | Carter ......................... 604/282 |
| 5,664,580 A * | 9/1997 | Erickson et al. ............. 600/585 |
| 5,685,868 A | 11/1997 | Lundquist .................... 604/280 |
| 5,695,482 A | 12/1997 | Kaldany ...................... 604/280 |
| 5,741,429 A | 4/1998 | Donadio, III et al. .......... 216/8 |
| 5,762,615 A * | 6/1998 | Weier |
| 5,827,242 A | 10/1998 | Follmer et al. .............. 604/282 |
| 5,911,715 A | 6/1999 | Berg et al. ................... 604/525 |
| 5,921,956 A | 7/1999 | Grinberg et al. .............. 604/95 |
| 5,957,903 A * | 9/1999 | Mirzaee et al. |
| 5,971,975 A | 10/1999 | Mills et al. .................. 604/527 |
| 5,972,441 A | 10/1999 | Campbell et al. ........... 428/34.1 |
| 5,984,877 A * | 11/1999 | Fleischhacker, Jr. |
| 6,007,478 A | 12/1999 | Siess et al. ................... 600/16 |
| 6,056,702 A * | 5/2000 | Lorenzo |

FOREIGN PATENT DOCUMENTS

| | | |
|---|---|---|
| EP | 0 608 853 A2 | 1/1994 |
| JP | 8257128 | 10/1996 |
| JP | 8308933 | 11/1996 |
| WO | WO 93/01855 | 2/1993 |
| WO | WO 93/04722 | 3/1993 |
| WO | WO 96/38193 | 12/1996 |
| WO | WO 98/58696 | 12/1998 |

* cited by examiner

Primary Examiner—Paul J. Hirsch
(74) Attorney, Agent, or Firm—Crompton, Seager & Tufte LLC

(57) ABSTRACT

A steerable guide wire and associated methods are disclosed. A guidewire in accordance with the present invention includes a shaft assembly including a lumen defined by a coil and an elongate shaft disposed within the lumen defined by the coil, a distal end of the coil being fixed to the elongate shaft proximate a distal end thereof, the elongate shaft including a curved portion proximate the distal end thereof, wherein the curved portion of the elongate shaft is biased to assume a substantially curved shape.

19 Claims, 7 Drawing Sheets

STEERABLE GUIDEWIRE

FIELD OF THE INVENTION

The present invention relates generally to intravascular guidewires. More particularly, the present invention relates to steerable guidewires.

BACKGROUND OF THE INVENTION

Intravascular catheters are currently utilized in a wide variety of minimally-invasive medical procedures. Generally, an intravascular catheter enables a physician to remotely perform a medical procedure by inserting the catheter into the vascular system of the patient at an easily accessible location and urging the catheter forward through the vasculature until the tip of the catheter is proximate a desirable target site. By this method, virtually any target site in the patient's vascular system may be remotely accessed, including the coronary, cerebral, and peripheral vasculature.

A physician attempting to position a catheter within a patient's vascular system may encounter a number of challenges. For example, the target site may be located a relatively long distance from the access site. By way of a second example, the path taken by a catheter through the vascular system may be tortuous, requiring the catheter to change direction frequently. In some cases, it may even be necessary for the catheter to double back on itself. A guidewire may be utilized to aid in advancing a catheter through the vasculature of a patient.

A guidewire may be inserted into the vascular system of the patient at an easily accessible location and urged forward through the vasculature until the tip of the guidewire is proximate a desirable target site. A proximal end of the guide wire may then be inserted into a guidewire lumen of a catheter. The tip of the catheter may be advanced along the length of the guidewire until it reaches a desirable target site.

SUMMARY OF THE INVENTION

The present invention relates generally to intravascular guidewires. More particularly, the present invention relates to steerable guidewires. A guidewire in accordance with one embodiment of the present invention includes a shaft assembly having a distal end and a proximate end. The shaft assembly includes a coil defining a lumen and a wire disposed in the lumen of coil. A distal end of coil is fixed to a tip member. Likewise, a distal end of the wire is fixed to tip member. The wire extends beyond a proximal end of the coil forming a proximal portion of the wire terminating at a proximal end of the wire.

In a presently preferred embodiment, the wire includes a curved portion disposed proximate the distal end of the shaft assembly. In this presently preferred embodiment, the curved portion of the wire urges the coil into a substantially curved shape. Also, in a presently preferred embodiment, the curved portion of wire is biased to return to a generally curved shape after being deflected.

In a method in accordance with the present invention, a guidewire may be inserted into the vascular system of a patient and urged forward through the vasculature until the tip member of the guidewire is proximate a desirable target site. As the guidewire is advanced through the vasculature of a patent, it may be necessary to "steer" the guidewire. For example, the distal end of the guidewire may reach a branch in the vasculature. The physician may direct the distal end of the guidewire toward the desired branch of the vasculature. Curved portion of wire may facilitate the steering process. Torsional forces may be applied to the proximal portion of the guidewire to alter the angular orientation of curved portion relative to the blood vessel. In this manner, the distal end of guidewire may be directed into the ostium of a desired vessel.

A method of steering a guidewire in accordance with the present invention may include the step of altering the curvature of distal portion of the guidewire. The step of altering the curvature of distal portion of the guidewire may be accomplished by urging a proximal portion of the wire proximally with respect to the proximal end of coil. Once the guidewire is positioned, the proximal end of guidewire may be inserted into a guidewire lumen of a catheter. The tip of the catheter may be advanced along the length of the guidewire until it reaches a desirable target site. In this manner, the guidewire aids the physician in delivering the distal tip of the catheter to the desired target site.

DETAILED DESCRIPTION OF THE INVENTION

The following detailed description should be read with reference to the drawings, in which like elements in different drawings are numbered in like fashion. The drawings which are not necessarily to scale, depict selected embodiments and are not intended to limit the scope of the invention. Examples of constructions, materials, dimensions, and manufacturing processes are provided for various elements. Those skilled in the art will recognize that many of the examples provided have suitable alternatives which may be utilized.

Figure 1:
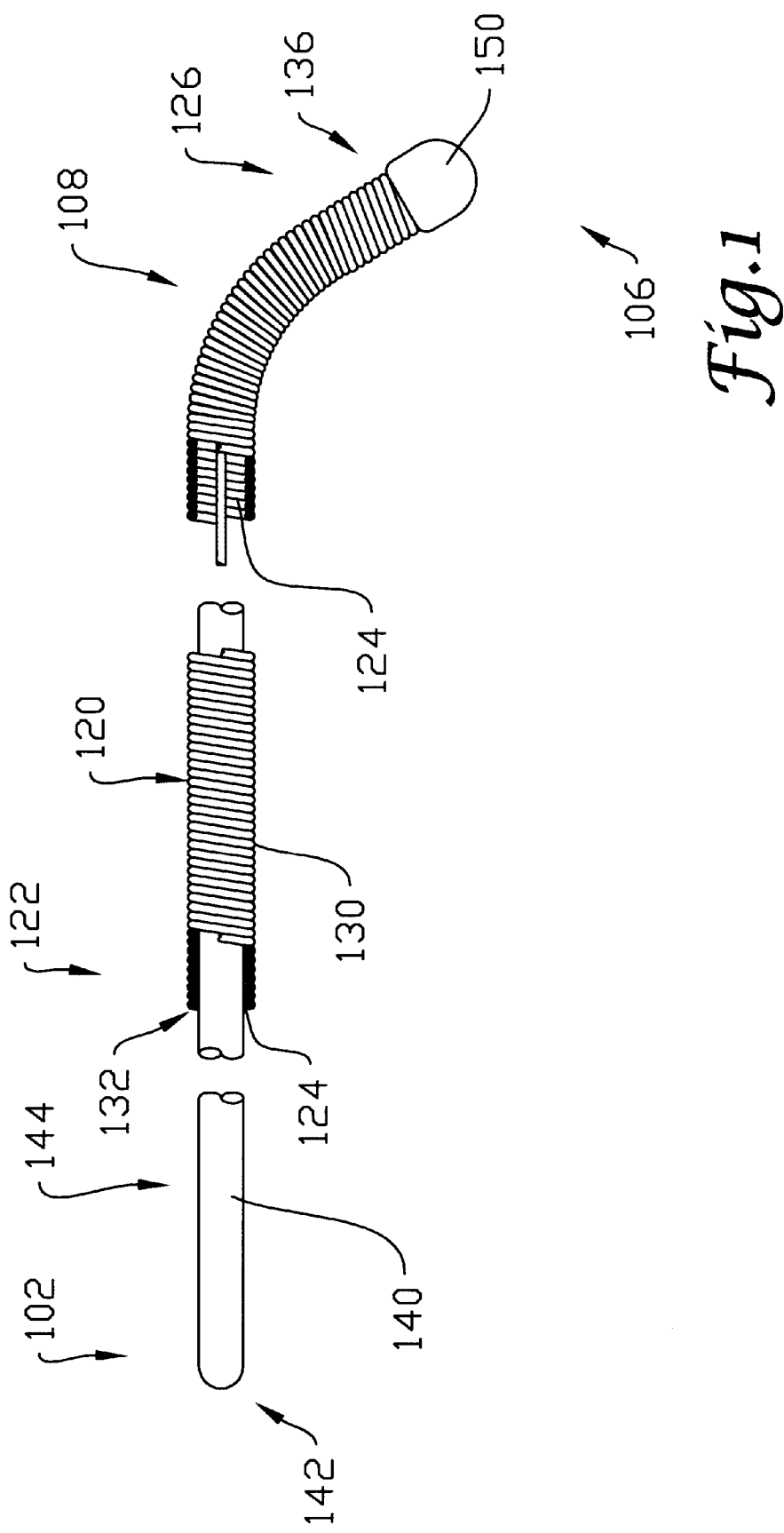
FIG. 1 is a plan view of a guidewire in accordance with an exemplary embodiment of the present invention.

FIG. 1 is a plan view of a guidewire 100 in accordance with the present invention. Guidewire 100 includes a distal end 106, a distal portion 108, and a proximal end 102. Guidewire 100 also includes a shaft assembly 120 having a distal end 126 and a proximate end 122. As shown in FIG. 1, shaft assembly 120 includes a coil 130 defining a lumen 124 and a wire 140 disposed in lumen 124 of coil 130. A distal end 136 of coil 130 is fixed to a tip member 150. Likewise, a distal end 146 (not shown) of wire 140 is fixed to tip member 150. Wire 140 extends beyond a proximal end 132 of coil 130 forming a proximal portion 144 of wire 140 terminating at a proximal end 142 of wire 140.

Figure 2:
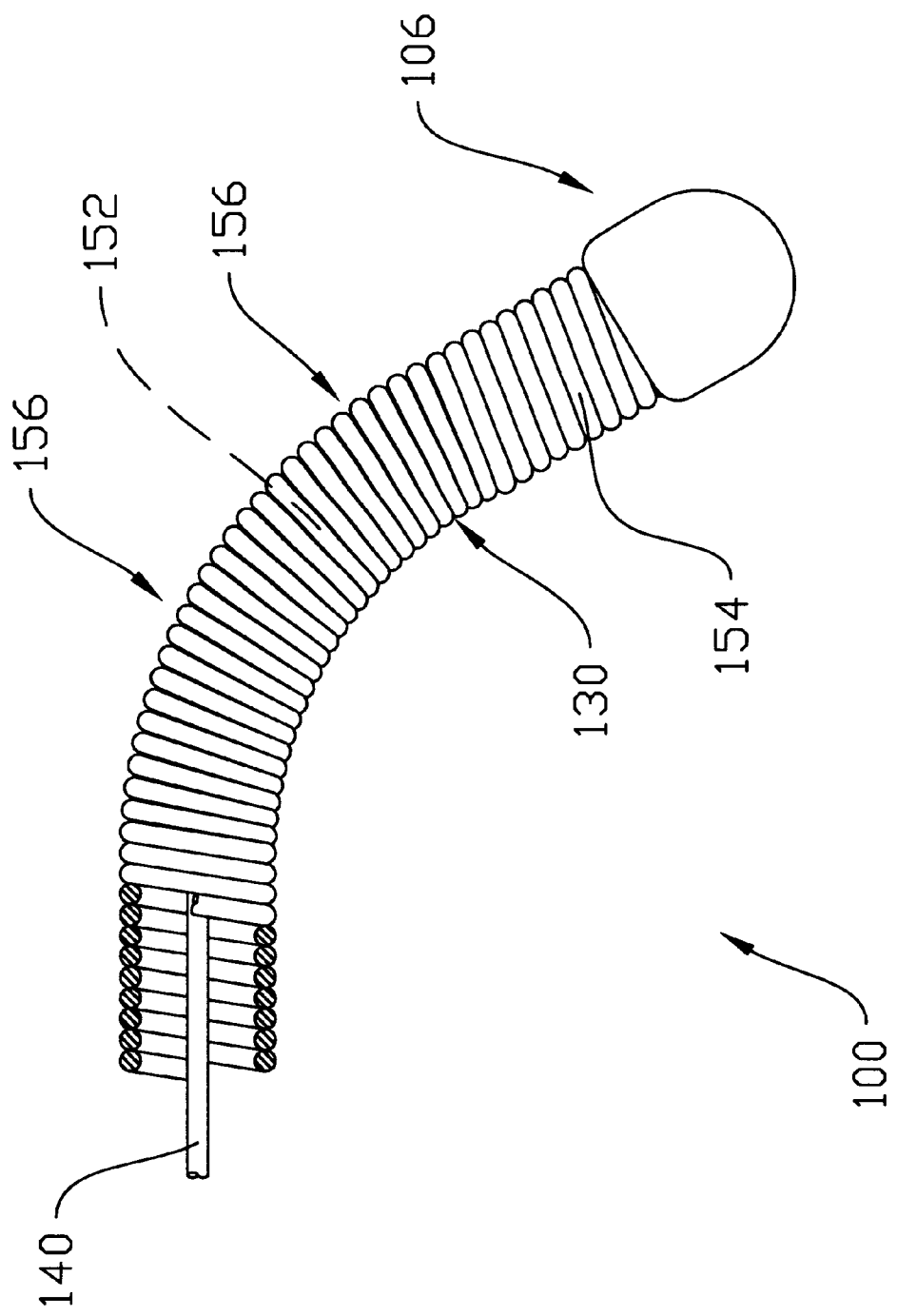
FIG. 2 is a plan view of a distal portion of a guidewire in accordance with an exemplary embodiment of the present invention.

FIG. 2 is a plan view of a distal portion of guidewire 100. Wire 140 of guidewire 100 includes a curved portion 152 disposed proximate distal end 106 of guidewire 100. In the embodiment of FIG. 1 and FIG. 2, curved portion 152 of wire 140 is shown in a substantially unbiased position. In the embodiment of FIG. 1 and FIG. 2, coil 130 is urged into a substantially curved shape by curved portion 152 of wire 140. In a presently preferred embodiment, curved portion 152 of wire 140 is biased to return to a generally curved shape after being deflected.

In FIG. 2, it may be appreciated that coil 130 is comprised of a plurality of turns 154. In the embodiment of FIG. 2, the longitudinal axis of coil 130 is disposed along a generally curved path. Also in the embodiment of FIG. 2, coil 130 defines a plurality of gaps 156 disposed between adjacent turns of coil 130. Those of skill in the art will appreciate that curved portion 152 of wire 140 may have any radius of curvature without deviating from the spirit and scope of the present invention. Likewise curved portion 152 may have any bend angle without deviating from the spirit and scope of the present invention.

Figure 3:
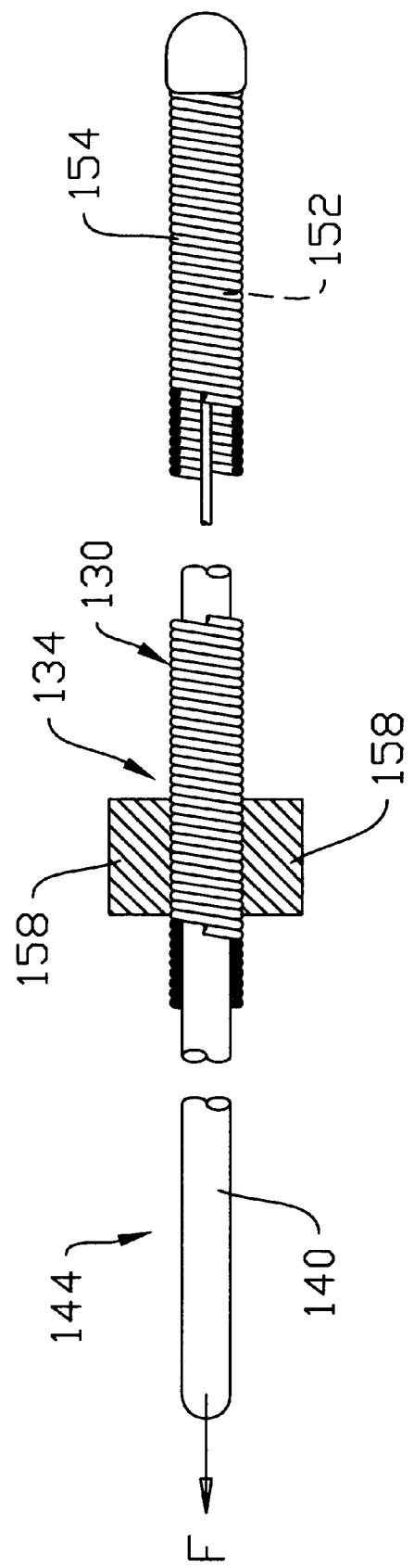
FIG. 3 is a plan view of a guidewire in accordance with an exemplary embodiment of the present invention, in the embodiment of FIG. 3, a plurality of grabbers are disposed about a proximal portion of a coil of the guidewire and a force F is acting upon a proximal portion of a wire of the guidewire in accordance with a method of the present invention.

FIG. 3 is a plan view of guidewire 100. In the embodiment of FIG. 3, a plurality of grabbers 158 are disposed about a proximal portion 134 of coil 130. Also in the embodiment of FIG. 3, a force F is acting upon proximal portion 144 of wire 140. As described previously, curved portion 152 of wire 140 is biased to assume a generally curved shape. In the embodiment of FIG. 3, the application of force F to proximal portion 144 of wire 140 has urged turns 154 of coil 130 into close proximity with each other, and urged wire 140 into a substantially straightened state.

Methods in accordance with the present invention have been envisioned in which coil 130 is grasped with two or more digits of a physicians hand, and a pulling force is applied to proximal portion 144 of wire 140 utilizing a second hand of the physician. For example, a physician could grasp proximal portion 134 of coil 130 with the thumb and index finger of her left hand. Also in this example, the physician could grasp proximal portion 144 of wire 140 with the thumb and index finger of her right hand. The physician could then urge proximal portion 144 of wire 140 proximally with respect to proximal portion 134 of coil 130. Embodiments of the present invention have been envisioned in which a plurality of turns 154 of proximal portion 134 of coil 130 are bonded together, for example, by soldering. In some applications, bonding the turns in this manner may produce a desired level of durability in proximal portion 134 of coil 130. Embodiments of the present invention have also been envisioned in which shaft assembly 120 further includes an elongate tubular member having a lumen, a proximal end, and a distal end. In this envisioned embodiment, proximal end 132 of coil 130 may be fixed to the distal end of the elongate tubular member, and wire 140 may be disposed within the lumen of the elongate tubular member.

In a method in accordance with the present invention, guidewire 100 may be inserted into the vascular system of a patient and urged forward through the vasculature until tip member 150 of guidewire 100 is proximate a desirable target site. As guidewire 100 is advanced through the vasculature of a patent, it may be necessary to "steer" the guidewire. For example, the distal end of guidewire 100 may reach a branch in the vasculature. The physician may direct the distal end of the guidewire toward the desired branch of the vasculature. Curved portion 108 of guidewire 100 may facilitate the steering process. Torsional forces may be applied to the proximal portion of guidewire 100 to alter the angular orientation of curved portion 152 relative to the blood vessel. In this manner, the distal end of guidewire 100 may be directed into the ostium of a desired vessel.

With reference to FIG. 1 through FIG. 3, it may be appreciated that steering may also be facilitated by selectively altering the curvature of distal portion 108 of guidewire 100. A method of steering a guidewire in accordance with the present invention may include the step of altering the curvature of distal portion 108 of guidewire 100. The step of altering the curvature of distal portion 108 of guidewire 100 may be accomplished by urging proximal portion 144 of wire 140 proximally with respect to proximal end 132 of coil 130.

Once guidewire 100 is positioned, proximal end 102 of guidewire 100 may be inserted into a guidewire lumen of a catheter. The tip of the catheter may be advanced along the length of the guidewire until it reaches a desirable target site. In this manner, guidewire 100 may aid a physician in delivering the distal tip of a catheter to a desired target site.

The term "wire", as used in describing wire 140 should not be mistaken as limiting wire 140 to elements having a circular cross section. The cross section of wire 140 may be any number of shapes. For example, the cross section of wire 140 could be rectangular, elliptical, etc. Likewise, the term "wire", as used in describing wire 140 should not be mistaken as being limited to metallic materials. In fact, wire 140 may comprise many metallic and non-metallic materials. Examples of metallic materials which may be suitable in some applications include stainless steel, tantalum, and titanium. Wire 140 may also include a nickel-titanium alloy known in the art as Nitinol. Nitinol is commercially available from Memry Technologies (Brookfield, Conn.), TiNi Alloy Company (San Leandro, Calif.), and Shape Memory Applications (Sunnyvale, Calif.). Examples of non-metallic materials which may be suitable in some applications may be found in the list immediately below which is not exhaustive: polycarbonate, poly(L-lactide) (PLLA), poly(D,L-lactide) (PLA), polyglycolide (PGA), poly(L-lactide-co-D, L-lactide) (PLLA/PLA), poly(L-lactide-co-glycolide) (PLLA/PGA), poly(D, L-lactide-co-glycolide) (PLA/PGA), poly(glycolide-co-trimethylene carbonate) (PGA/PTMC), polyethylene oxide (PEO), polydioxanone (PDS), polycaprolactone (PCL), polyhydroxylbutyrate (PHBT), poly (phosphazene), polyD,L-lactide-co-caprolactone) (PLA/PCL), poly(glycolide-co-caprolactone) (PGA/PCL), polyanhydrides (PAN), poly(ortho esters), poly(phoshate ester), poly(amino acid), poly(hydroxy butyrate), polyacrylate, polyacrylamid, poly(hydroxyethyl methacrylate), polyurethane, polysiloxane and their copolymers. Embodiments of the present invention have also been envisioned in which wire 140 has a tubular cross section. For example, wire 140 may comprise Nitinol hypodermic tubing.

Figure 4:
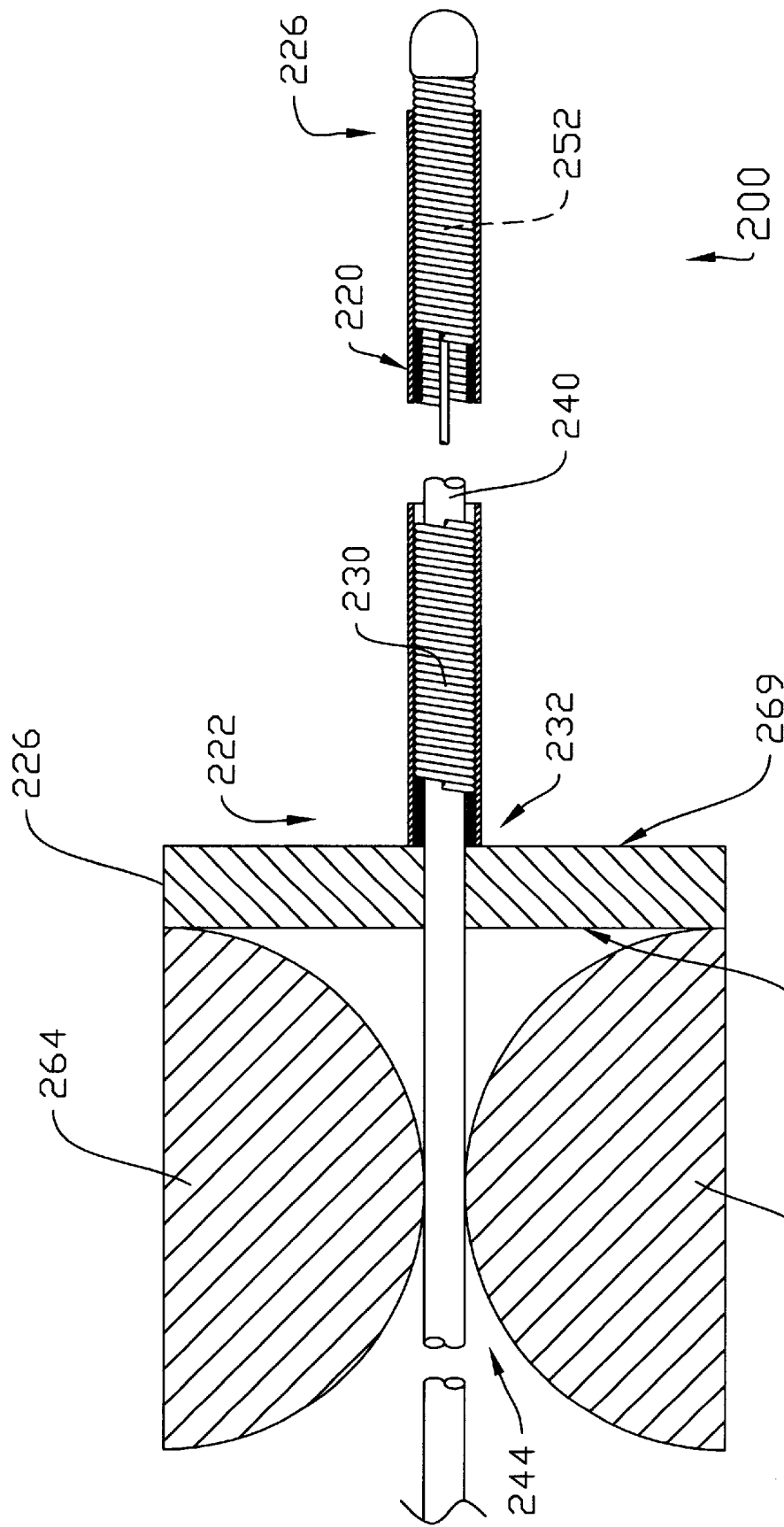
FIG. 4 is a plan view of a guidewire in accordance with an exemplary embodiment of the present invention.

FIG. 4 is a plan view of a guidewire 200 in accordance with the present invention. Guidewire 200 includes an elongate shaft assembly 220 having a distal end 226 and a proximate end 222. The construction of shaft assembly 220 is best shown in FIG. 5.

Figure 5:
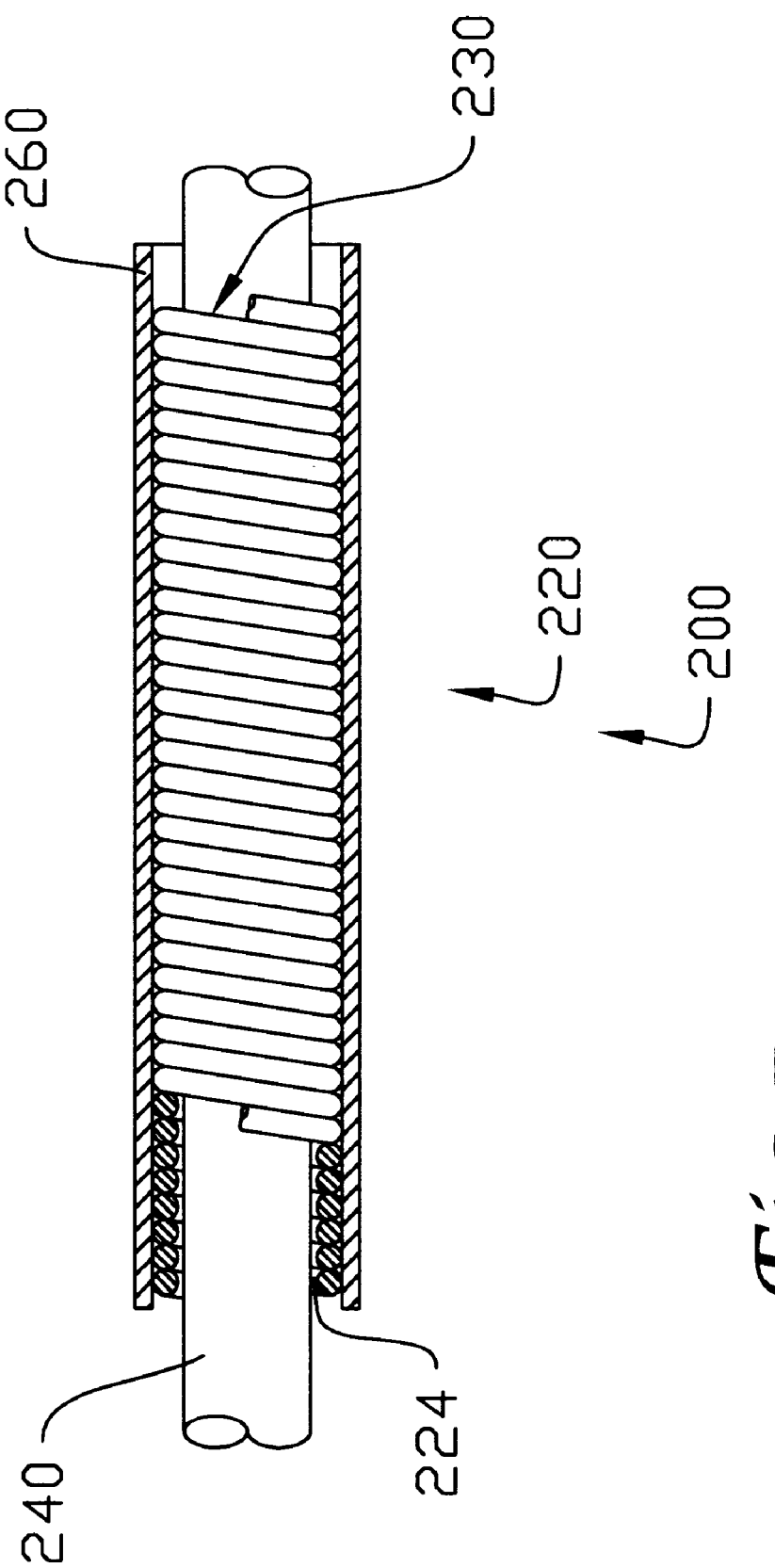
FIG. 5 is a partial cross sectional view of a shaft assembly in accordance with an exemplary embodiment of the present invention.

FIG. 5 is a partial cross sectional view of a portion of shaft assembly 220. As shown in FIG. 5, shaft assembly 220 includes a sheath 260 disposed about a coil 230. Shaft assembly 220 also includes a lumen 224. A wire 240 is disposed in lumen 224 of shaft assembly 220. In a presently preferred embodiment, sheath 260 is comprised of polytetrafluoroethylene (PTFE) heat shrink tubing. Suitable PTFE heat shrink tubing is commercially available from Zeus Industries of Orangeburg, S.C. and Raychem Corporation of Menlo Park, Calif. Those of skill in the art will appreciate that sheath 260 may be comprised other materials without deviating from the spirit and scope of the present invention. Examples of materials which may be suitable in some applications include: polyethylene (PE), polypropylene (PP), polyvinylchloride (PVC), polyurethane, and polyether block amide (PEBA)

Additional embodiments of shaft assembly 220 have been contemplated. One envisioned embodiment includes a first sheath disposed about coil 230, and a second sheet disposed within a lumen defined by coil 230. A second envisioned embodiment includes coil 230 and an inner sheath disposed between coil 230 and wire 240, which is disposed within lumen 224 of shaft assembly 220. Finally, embodiments of shaft assembly 220 have been envisioned in which coil 230 comprises a core wire, and an outer layer disposed about the core wire. The core wire may comprise various materials without deviating from the spirit and scope of the present invention. Examples of materials which may be suitable in some applications, include: stainless steel, nickel titanium alloy, and platinum. Likewise, the outer layer may comprise various materials without deviating from the spirit and scope of the present invention. Examples of materials which may be suitable in some applications include: polyethylene, polypropylene, and PTFE.

Referring again to FIG. 4, a steering fixture 262 is disposed about wire 240 proximate proximal end 232 of coil 230. In the embodiment of FIG. 4, a proximal portion 244 of wire 240 is pinched between a first digit 264 and a second digit 266. First digit 264 and second digit 266 are both seated against a proximal surface 268 of steering fixture 262. A distal surface 269 of steering fixture 262 is seated against proximal end 232 of coil 230. Embodiments of the present invention have also been envisioned in which shaft assembly 220 further includes an elongate tubular member having a lumen, a proximal end, and a distal end. In this envisioned embodiment, proximal end 232 of coil 230 may be fixed to the distal end of the elongate tubular member, and wire 240 may be disposed within the lumen of the elongate tubular member. Also in this envisioned embodiment, distal surface 269 of steering fixture 262 may be seated against the proximal end of the elongate tubular member.

As in the previous embodiment, wire 240 includes a curved portion 252 which is biased to return to a curved shape. In the embodiment of FIG. 4 first digit 264, second digit 266, and steering fixture 262 are arranged to hold wire 240 in position relative to coil 230. It may be appreciated that when wire 240 is held in position relative to coil 230, curved portion 252 of wire 240 is held in a substantially straight position.

Figure 6:
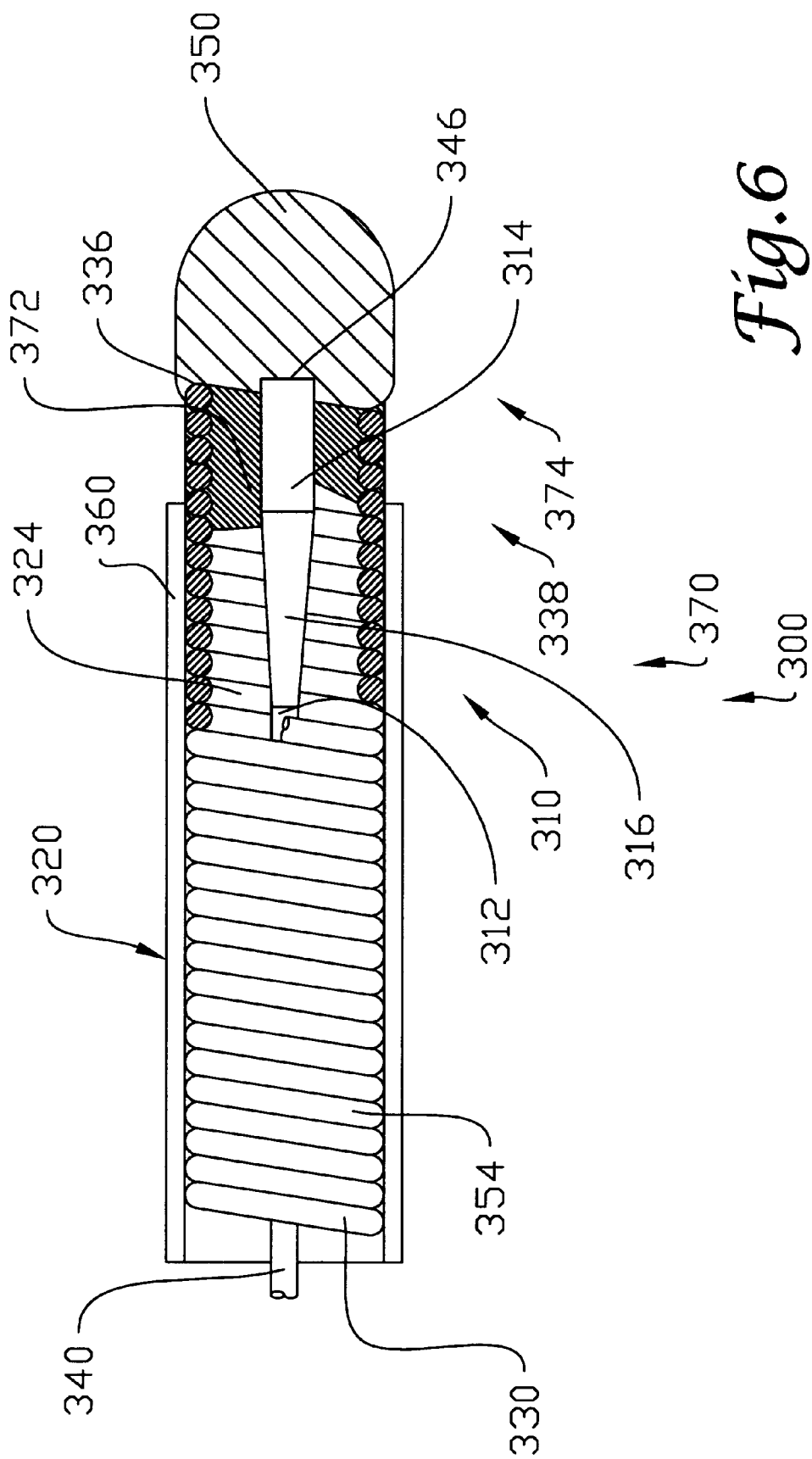
FIG. 6 is a cross-sectional view of a tip portion of a guidewire in accordance with an exemplary embodiment of the present invention.

FIG. 6 is a cross-sectional view of a tip portion 370 of a guidewire 300 in accordance with the present invention. In the embodiment of FIG. 6, guidewire 300 includes a shaft assembly 320 comprising a sheath 360 disposed about a coil 330, and a wire 340 disposed within a lumen 324 defined by coil 330. A tip member 350 is fixed to a distal end 346 of wire 340 and a distal end 336 of coil 330. In the embodiment of FIG. 6, a joint 372 connects a tip portion 374 of wire 340 to a tip portion 338 of coil 330 over a plurality of turns 354. In a presently preferred embodiment, joint 372 is comprised of solder. Those of skill in the art will appreciate that joint 372 may be comprised of other materials without deviating from the spirit and scope of the present invention. It should also be appreciated that a variety of joining methods may be utilized without deviating from the spirit and scope of the present invention. Examples of joining methods which may be suitable in some applications include soldering, brazing, welding, and adhesive bonding. Examples of welding processes which may be suitable in some applications include LASER welding, TIG welding, resistance welding, and plasma welding.

In FIG. 6, it may be appreciated that wire 340 includes a profiled portion 310. In the embodiment of FIG. 6, profiled portion 310 includes a first diameter 312, a second diameter 314, and a taper 316. Those of skill in the art will appreciate that wire 340 may include a plurality of diameters and a plurality of tapers without deviating from the spirit and scope of the present invention.

Figure 7:
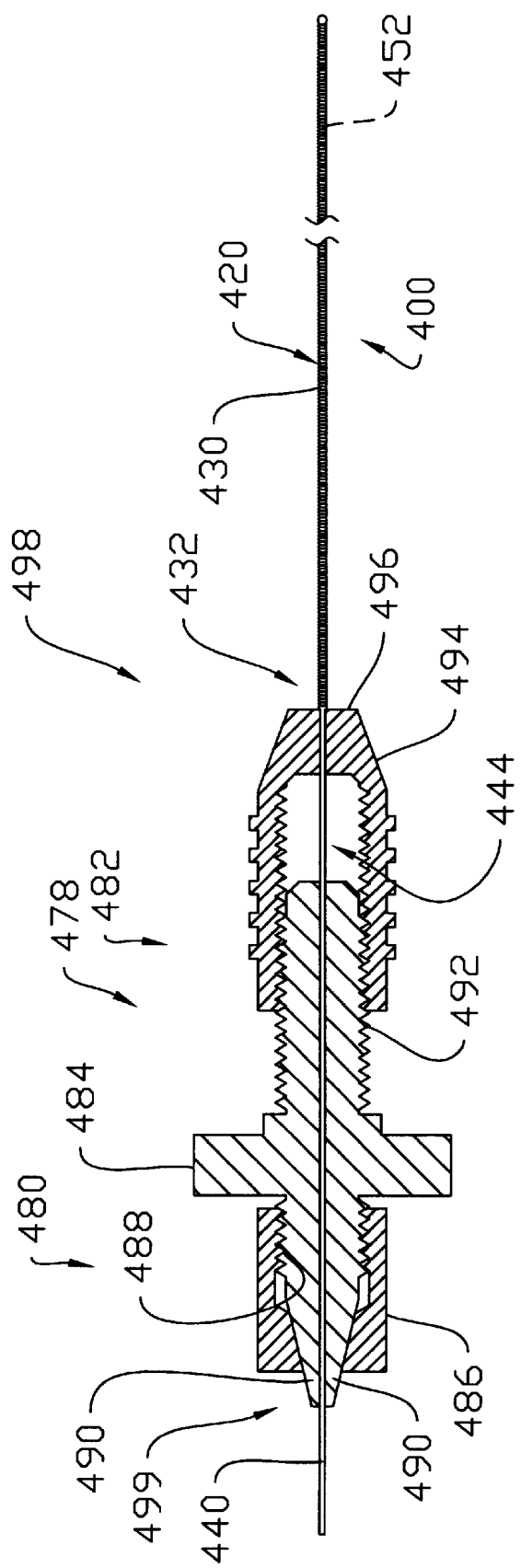
FIG. 7 is a plan view of a guidewire system including a guidewire having a distal portion, and a steering mechanism adapted to alter the shape of the distal portion of the guidewire in accordance with an exemplary embodiment of the present invention.

FIG. 7 is a plan view of a guidewire system 476 in accordance with the present invention. Guidewire system 476 includes guidewire 400 including a shaft assembly 420. Shaft assembly 420 includes a coil 430 defining a lumen and a wire 440 slidingly disposed within the lumen of coil 430. A steering mechanism 478 is disposed about wire 440 proximate a proximal end 432 of coil 430.

In the embodiment of FIG. 7, steering mechanism 478 includes a wire lock 480, a length adjustment 482, and an arbor 484. Arbor 484 includes a distal end 498 and a proximal end 499. Wire lock 480 includes a proximal thread 488 and a plurality of jaws 490 defined by arbor 484. Wire lock 480 also includes an arbor nut 486 which is disposed in threaded engagement with proximal thread 488. In FIG. 7, it may be appreciated that a portion of arbor nut 486 is disposed about jaws 490. In a presently preferred embodiment, arbor nut 486 urges jaws 490 into grasping contact with wire 440 when arbor nut 486 is threadingly advanced onto proximal thread 488. Length adjustment 482 comprises a sleeve 494 and a distal thread 492 defined by arbor 484. In FIG. 7, it may be appreciated that sleeve 494 threadingly engages distal thread 492 and a distal surface 496 of sleeve 494 is seated against proximal end 432 of coil 430.

In the embodiment of FIG. 7, wire 440 includes a curved portion 452 (not shown) proximate the distal end thereof. In this presently preferred embodiment, curved portion 452 of wire 440 is biased to assume a generally curved shape. In the embodiment of FIG. 7, length adjustment 482 of steering mechanism 478 is arranged so that wire 440 assumes a substantially straight shape.

In a presently preferred embodiment, the linear position of sleeve 494 relative to arbor 484 may be selectively altered by rotating sleeve 494 relative to arbor 484. Altering the position of sleeve 494 relative to arbor 484 may alter the position of a proximal portion 444 of wire 440 relative to proximal end 432 of coil 430. In this presently preferred embodiment, the shape of wire 440 and coil 430 may be altered by adjusting the linear position of sleeve 494 relative to arbor 484.

A physician may utilize steering mechanism 478 to selectively alter the shape of a distal portion 408 of guidewire 400. Changes in the shape of distal portion 408 may assist in steering guidewire 400 through the vasculature of a patient. A method of steering a guidewire in accordance with the present invention may include the step of inserting proximal end 442 of wire 440 into steering mechanism 478. A method of steering a guidewire in accordance with the present invention may also include the step of fixing wire lock 480 to wire 440. A method of steering a guidewire in accordance with the present invention may additionally include the step of urging proximal portion 444 of wire 440 proximal with respect to proximal end 432 of coil 430. In the embodiment of FIG. 7, length adjustment 482 of steering mechanism 478 may be utilized to urge proximal portion 444 of wire 440 proximally with respect to proximal end 432 of coil 430.

Having thus described the figures, methods in accordance with the present invention may now be described with reference thereto. It should be understood that steps may be omitted from each process and/or the order of the steps may be changed without deviating from the spirit or scope of the invention. It is anticipated that in some applications, two or more steps may be performed more or less simultaneously to promote efficiency.

A method of fabricating a guidewire in accordance with the present invention may begin with the step providing an elongate shaft. In the embodiment of FIG. 1, the elongate shaft is comprised of a wire. With reference to FIG. 6, it may be appreciated that the wire may include a plurality of profiled portions.

A method in accordance with the present invention may include the step of removing material from an outer surface of an elongate shaft to produce a desired profile. Those of skill in the art will appreciate that many methods may be utilized to remove material from the outer surface of the elongate shaft. Examples of processes which may be suitable in some applications include grinding and turning on a lathe.

A method in accordance with the present invention may include the step of cutting a wire to a desired length. Those of skill in the art will appreciate that a variety of cutting processes may be utilized without deviating from the spirit and scope of the present invention. Examples of processes which may be suitable in some applications include electronic discharge machining (EDM), electro-chemical machining (ECM), water jet cutting, LASER cutting, abrasive cutting, and mechanical cutting utilizing a cutting tool to remove material.

A method in accordance with the present invention may include the step of forming a coil. The step of forming a coil may include the steps of extruding a wire, drawing the wire to a desired diameter, and winding the wire around a mandrel. The step of forming a coil may also include the step(s) of cutting the wire to length before and/or after the winding process.

A method in accordance with the present invention may include the step of inserting an elongate shaft into a lumen defined by the coil and fixing the elongate shaft to the coil proximate their distal ends. Those of skill in the art will appreciate that many fixing processes may be utilized without deviating from the spirit and scope of the present invention. Examples of fixing processes which may be suitable in some applications include welding, soldering, brazing, adhesive bonding, and the use of a mechanical fastener.

A method in accordance with the present invention may include the step of forming a tip member. One method of forming a tip member includes the steps of depositing metal proximate a distal end of the coil and a distal end of the wire. Examples of material deposition processes which may be suitable in some applications include soldering, brazing, over-molding, and resin casting.

A method in accordance with the present invention may include the step of inserting a shaft assembly into the lumen of a sheath. In a presently preferred method, the sheath may be comprised of shrink tubing. A method in accordance with the present invention may include the step of heating the sheath and causing it to shrink. A number of methods may be used to apply heat to the sheath including convection, conduction and radiation. An example of heating with radiant energy is directing infrared energy from an infrared heat source at the material. Infrared energy sources suitable for this process are commercially available from Research Incorporated of Minnetonka, Minn. An example of heating with convection is directing a flow of hot air from a hot air gun so that it impinges on the material. Hot air guns suitable for this application are commercially available from Leister Elektro-Geratebau of Lucerne, Switzerland.

Having thus described the preferred embodiments of the present invention, those of skill in the art will readily appreciate that yet other embodiments may be made and used within the scope of the claims hereto attached. Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. A steerable guidewire, comprising:
   a shaft assembly including a lumen defined by a coil and an elongate shaft disposed within the lumen defined by the coil;
   a distal end of the coil being fixed to the elongate shaft proximate a distal end thereof;
   the elongate shaft including a curved portion proximate the distal end thereof; and
   wherein the curved portion of the elongate shaft is biased to assume a substantially curved shape and wherein the curved portion of the wire assumes a substantially straight position when a proximal end of the elongate shaft is urged proximally relative to a proximal end of the coil.

2. The guidewire of claim 1, wherein the distal end of the coil is fixed to the elongate shaft proximate the distal end thereof by a weld joint.

3. The guidewire of claim 1, further including a solder joint disposed between the elongate shaft and the coil.

4. The guidewire of claim 1, wherein the elongate shaft comprises a wire including a nickel titanium alloy.

5. The guidewire of claim 1, wherein the elongate shaft comprises a ribbon wire.

6. The guidewire of claim 1, further including a sheath disposed about the coil.

7. The guidewire of claim 1, further including a sheath disposed about the coil;
   wherein the sheath comprises polytetrafluoroethylene heat shrink tubing.

8. The guidewire of claim 1, wherein the coil comprises a wire including a jacket disposed thereabout.

9. The guidewire of claim 1, wherein the coil comprises a wire including a jacket disposed thereabout; and
   the jacket comprises polytetrafluoroethylene.

10. A steerable guidewire, comprising:
    a shaft assembly including a lumen defined by a coil and an elongate shaft disposed within the lumen defined by the coil;
    a distal end of the coil being fixed to the elongate shaft proximate a distal end thereof;

the elongate shaft including a curved portion proximate the distal end thereof;

wherein the curved portion of the elongate shaft is biased to assume a substantially curved shape; and wherein the curved portion of the wire assumes a substantially straight position when a proximal end of the elongate shaft is urged proximally relative to a proximal end of the coil.

11. The guidewire of claim 10, wherein the distal end of the coil is fixed to the elongate shaft proximate the distal end thereof by a weld joint.

12. The guidewire of claim 10, further including a solder joint disposed between the elongate shaft and the coil.

13. The guidewire of claim 10, wherein the elongate shaft comprises a wire including a nickel titanium alloy.

14. The guidewire of claim 10, wherein the elongate shaft comprises a ribbon wire.

15. The guidewire of claim 10, further including a sheath disposed about the coil.

16. The guidewire of claim 10, further including a sheath disposed about the coil;

wherein the sheath comprises polytetrafluoroethylene heat shrink tubing.

17. The guidewire of claim 10, wherein the coil comprises a wire including a jacket disposed thereabout.

18. The guidewire of claim 10, wherein the coil comprises a wire including a jacket disposed thereabout; and the jacket comprises polytetrafluoroethylene.

19. A steerable guidewire, comprising:

an elongate shaft having a distal end and a proximal end;

a plurality of rings disposed about the elongate shaft;

a distal most ring being fixed to the elongate shaft proximate the distal end thereof;

the elongate shaft including a curved portion proximate the distal end thereof;

wherein the curved portion of the elongate shaft is biased to assume a substantially curved shape; and wherein the curved portion of the wire assumes a substantially straight position when the proximal end of the elongate shaft is urged proximally relative to a proximal most ring of the guidewire.

\* \* \* \* \*